(12) United States Patent
Windheuser et al.

(10) Patent No.: US 9,314,359 B2
(45) Date of Patent: Apr. 19, 2016

(54) STENT DELIVERY SYSTEM (71) Applicant: Boston Scientific Scimed, Inc., Maple Grove, MN (US)

(72) Inventors: James E. Windheuser, Hopkinton, MA (US); Scott A. Davis, Southborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 40 days.

(21) Appl. No.: 14/208,907

(22) Filed: Mar. 13, 2014

(65) Prior Publication Data

US 2014/0277564 A1 Sep. 18, 2014

Related U.S. Application Data (60) Provisional application No. 61/787,914, filed on Mar. 15, 2013.

(51) Int. Cl.
| | |
|---|---|
| *A61F 2/04* | (2013.01) |
| *A61M 5/00* | (2006.01) |
| *A61F 2/966* | (2013.01) |
| *A61M 25/01* | (2006.01) |
| *A61M 25/04* | (2006.01) |

(Continued)

(52) U.S. Cl.
CPC .............. *A61F 2/966* (2013.01); *A61F 2/962* (2013.01); *A61M 25/01* (2013.01); *A61M 25/04* (2013.01); *A61M 27/002* (2013.01); *A61F 2/04* (2013.01); *A61F 2002/041* (2013.01); *A61M 2025/006* (2013.01); *A61M 2025/0006* (2013.01); *A61M 2025/0175* (2013.01); *A61M 2025/0681* (2013.01); *A61M 2210/1078* (2013.01); *A61M 2210/1082* (2013.01)

(58) Field of Classification Search
CPC .............. A61M 1/00; A61M 5/00; A61F 2/04
USPC .............................. 604/8, 540; 623/1.11, 23.7
See application file for complete search history.

(56) References Cited

U.S. PATENT DOCUMENTS

| | | | |
|---|---|---|---|
| 5,152,749 | A | 10/1992 | Giesy et al. |
| 5,334,185 | A | 8/1994 | Giesy et al. |

(Continued)

FOREIGN PATENT DOCUMENTS

| | | |
|---|---|---|
| EP | 0 79 26 57 A2 | 2/1997 |
| EP | 1314404 A2 | 5/2003 |

(Continued)

*Primary Examiner* — Suzette J Gherbi
(74) *Attorney, Agent, or Firm* — Kacvinsky Daisak Bluni PLLC (57) ABSTRACT An stent delivery system may include a delivery device and a tubular body having a lumen sized to slidably fit about an outer diameter of the delivery device and a drainage stent having an anchoring mechanism, wherein the delivery device includes a constraining member configured to engage an external portion of the tubular body at the proximal end of the delivery device. A method of delivering a stent may include inserting a tubular body into the port of an endoscope, inserting a stent delivery device and a stent having an anchoring mechanism into the tubular body, wherein the delivery device includes a constraining member configured to engage and retain the tubular body at the proximal end of the delivery device, advancing the drainage stent distally through the tubular body, sliding the tubular body proximally, and engaging an external portion of the tubular body with the constraining member.

18 Claims, 7 Drawing Sheets

(51) Int. Cl.
*A61M 27/00* (2006.01)
*A61F 2/962* (2013.01)
*A61M 25/00* (2006.01)
*A61M 25/06* (2006.01)

(56) References Cited

U.S. PATENT DOCUMENTS

| | | | |
|---|---|---|---|
| 5,772,609 | A | 6/1998 | Nguyen et al. |
| 5,921,952 | A | 7/1999 | Desmond, III et al. |
| 6,033,413 | A * | 3/2000 | Mikus et al. .................. 606/108 |
| 6,139,510 | A | 10/2000 | Palermo |
| 6,248,100 | B1 | 6/2001 | de Toledo et al. |
| 6,264,624 | B1 * | 7/2001 | Desmond et al. ................. 604/8 |
| 6,346,093 | B1 * | 2/2002 | Allman et al. ........... 604/167.06 |
| 6,562,024 | B2 * | 5/2003 | Alvarez de Toledo et al. ............................. 604/540 |
| 6,858,034 | B1 | 2/2005 | Hijlkema et al. |
| 8,298,276 | B2 | 10/2012 | Ozawa et al. |
| 2002/0007206 | A1 | 1/2002 | Bui et al. |
| 2005/0085892 | A1 | 4/2005 | Goto et al. |
| 2006/0162731 | A1 | 7/2006 | Wondka et al. |
| 2009/0024084 | A1 | 1/2009 | Khosla et al. |
| 2011/0071621 | A1 | 3/2011 | Griego et al. |
| 2012/0095567 | A1 | 4/2012 | Weisman et al. |
| 2012/0150070 | A1 * | 6/2012 | Ryan et al. .................... 600/567 |
| 2012/0203325 | A1 | 8/2012 | Weisman et al. |
| 2012/0330397 | A1 | 12/2012 | Harrison et al. |
| 2013/0030416 | A1 | 1/2013 | Fernandes et al. |
| 2013/0310833 | A1 * | 11/2013 | Brown et al. .................... 606/45 |
| 2014/0236064 | A1 * | 8/2014 | Binmoeller et al. ............. 604/8 |

FOREIGN PATENT DOCUMENTS

| | | |
|---|---|---|
| EP | 2067454 A1 | 10/2009 |
| WO | 9748343 A1 | 12/1997 |
| WO | 9959664 A1 | 11/1999 |
| WO | 2010138277 A1 | 12/2010 |

\* cited by examiner

STENT DELIVERY SYSTEM

REFERENCE TO RELATED APPLICATIONS

This application claims priority under 35 U.S.C. §119(e) to U.S. Provisional Application No. 61/787,914, filed Mar. 15, 2013, the entire disclosure of which is herein incorporated by reference.

FIELD OF THE INVENTION

The present invention pertains to medical devices and methods for using medical devices. More particularly, the present invention pertains to medical devices for delivering stents to the biliary tract and/or the pancreatic tract.

BACKGROUND

A wide variety of intraluminal medical devices have been developed for medical use, for example, use in the biliary tract. Some of these devices include guidewires, catheters, stents, and the like. These devices may be used according to any one of a variety of methods. Of the known medical devices and methods, each has certain advantages and disadvantages. There is an ongoing need to provide alternative medical devices as well as alternative methods for using medical devices.

BRIEF SUMMARY

An example drainage stent delivery system may include a drainage stent delivery device including a distal end and a handle disposed at a proximal end thereof; and a tubular body having a proximal end, a distal end, and a lumen extending therebetween, the lumen being sized to slidably fit about an outer diameter of the delivery device and an outer diameter of a drainage stent having an anchoring mechanism, the drainage stent disposed at the distal end of the delivery device; wherein the delivery device includes a constraining member configured to engage an external portion of the tubular body at the proximal end of the delivery device.

An example method of delivering a drainage stent may include inserting an endoscope including a port proximate a proximal end thereof into a patient; inserting a distal end of a tubular body into the port; inserting a distal end of a drainage stent delivery device and a drainage stent having an anchoring mechanism disposed at the distal end of the delivery device into the tubular body; wherein the delivery device includes a handle disposed at a proximal end thereof and includes a constraining member configured to engage and retain the tubular body at the proximal end of the delivery device; wherein the tubular body includes a lumen sized to slidably fit about an outer diameter of the delivery device and an outer diameter of the drainage stent having an anchoring mechanism; advancing the drainage stent distally through the tubular body; sliding the tubular body proximally toward the handle; and engaging an external portion of the tubular body with the constraining member.

A drainage stent delivery system may include a guidewire; an elongate pusher shaft including a proximal end, a distal end, and a lumen extending therebetween; wherein the guidewire is slidably disposed within the lumen of the pusher shaft; a drainage stent having an anchoring mechanism, the drainage stent disposed in abutting contact with the distal end of the pusher shaft; and a tubular body fixedly attached to an outer surface of the pusher shaft at the distal end; wherein the tubular body extends distally of the distal end of the pusher shaft and covers a proximal portion of the anchoring mechanism.

The above summary of some embodiments is not intended to describe each disclosed embodiment or every implementation of the present invention. The Figures and Detailed Description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

Weight percent, percent by weight, wt %, wt-%, % by weight, and the like are synonyms that refer to the concentration of a substance as the weight of that substance divided by the weight of the composition and multiplied by 100.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

A wide variety of biliary, endoscopic, and/or endosurgical procedures have been developed for making medical treatments, diagnoses, and images of areas along the biliary tract and/or the pancreatic tract. For the purposes of this disclosure, the "biliary tract" and/or the "pancreatic tract" are understood to include various components of the digestive system and include, for example, the various ducts of the biliary tree between the liver and the duodenum as well as the various ducts between the pancreas and the duodenum. Numerous endoscopic and/or endosurgical devices have been developed for making medical treatments, diagnoses, and images of areas along the biliary and pancreatic tracts. Some of these device and/or procedures include biliary catheters, biliary guidewires, biliary stent delivery systems, and the like. In general, these devices are guided to the biliary and/or pancreatic tract by an endoscope (and/or a duodenoscope, sheath, guide tube, catheter, etc.) that is disposed in the duodenum. Once positioned, various interventions can be performed depending on the needs of the patient and the type of device utilized. Other locations and/or uses are also contemplated for the systems disclosed herein including, for example, urinary tract interventions and/or urological interventions, gynecological interventions, etc.

Figure 1:
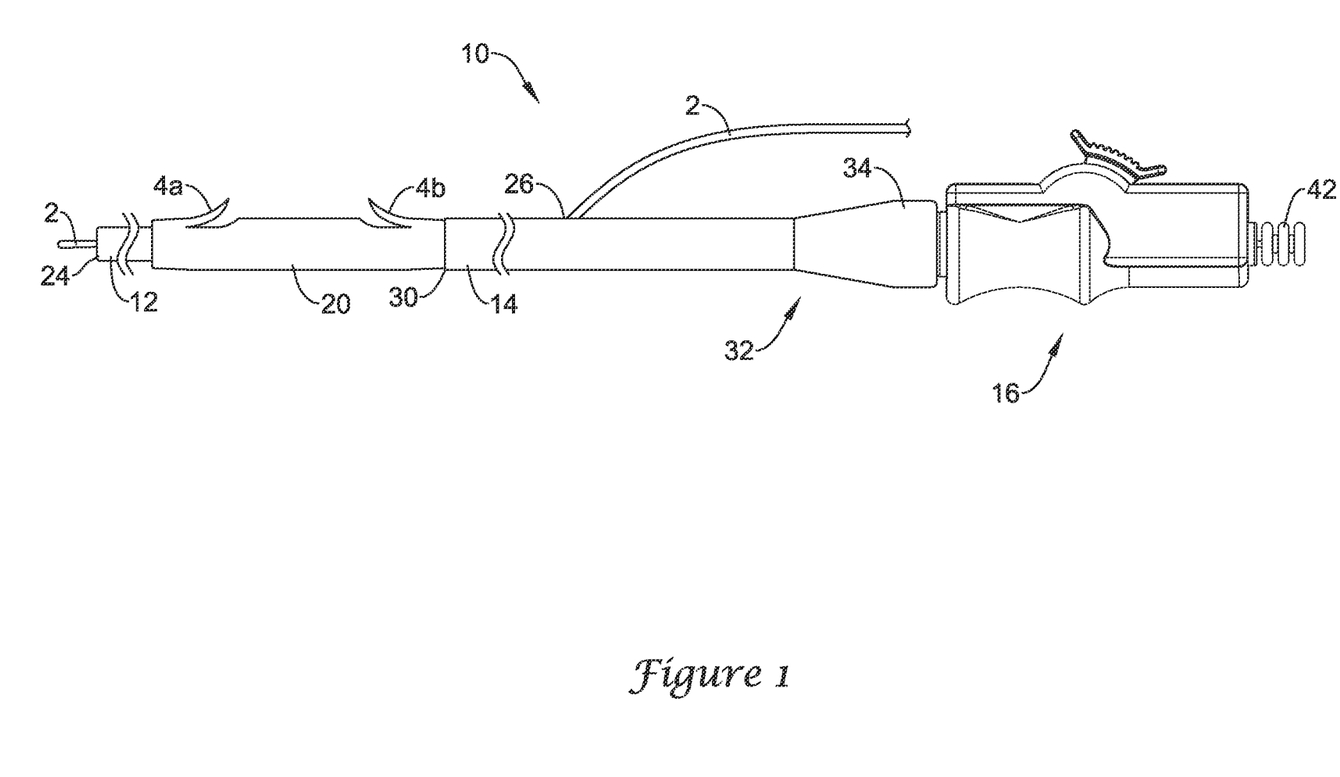
FIG. 1 is a partial side view of an example stent delivery system.
Figure 2:
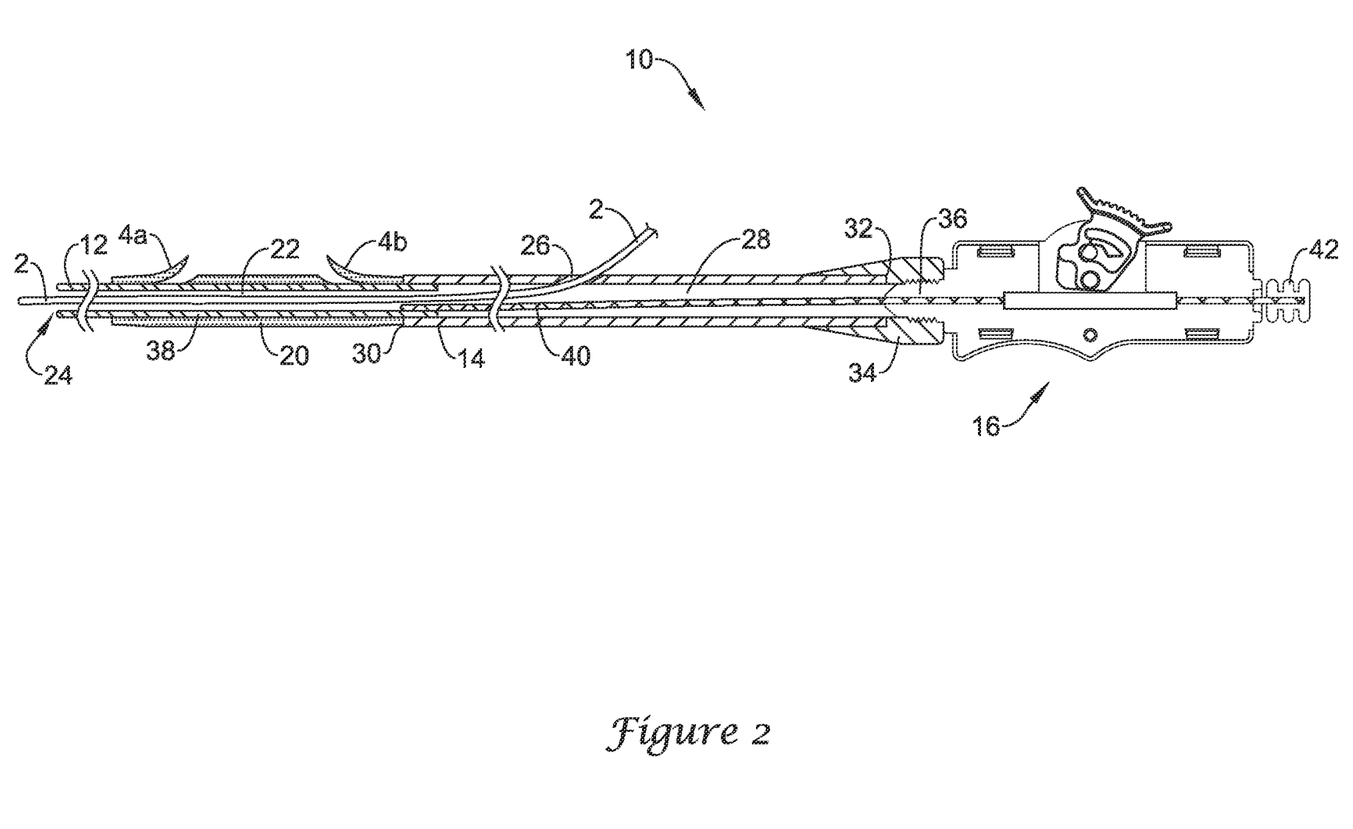
FIG. 2 is a partial cross-sectional view of an example stent delivery system.

Referring now to FIGS. 1 and 2, there is shown an example drainage stent delivery system, illustrated as including a catheter and/or delivery device 10 that may be used, for example, for delivering a stent 20 such as a drainage stent to a suitable target site such as, for example, a target site along the biliary and/or pancreatic tree. The delivery device 10 may also be used at any other suitable location. The stent 20 may be used to bypass or drain an obstructed lumen, for example along the biliary and/or pancreatic tree, and can be configured for long-term positioning within the body. It should be understood that the terms "drainage stent", "drainage catheter", and "stent" can be used interchangeably with reference to the devices and systems disclosed herein. In at least some embodiments, the stent 20 may include an anchoring system such as one or more barbs or flaps formed therein, for example a first or distal flap 4a and a second or proximal flap 4b. The flaps 4a/4b may help to secure the stent 20 within the anatomy (i.e., the biliary tract, the pancreatic tract, etc.) when the stent 20 is deployed. In some embodiments, additional distal and/or proximal flaps may be provided. Other embodiments are contemplated where other anchoring systems are utilized. These other anchoring systems may be used instead of the flaps 4a/4b or in addition to the flaps 4a/4b.

The delivery device 10 may be designed for use with a conventional guidewire 2 and may include a guide catheter 12, a push catheter 14, and a handle assembly 16. The guidewire 2 may extend into a lumen 22 of the guide catheter 12, through a distal guidewire port 24, and out a proximal guidewire port 26 formed in a sidewall of the push catheter 14 to a position where the guidewire 2 extends along the outer surface of the delivery device 10. In at least some embodiments, the proximal guidewire port 26 may be disposed adjacent to a proximal end 32 of the push catheter 14 such that the delivery device 10 is a "long wire" device. As the name implies, long wire devices utilize relatively long guidewires that extend along nearly the full length of the push catheter 14 and exit the proximal guidewire port 26, which is positioned near the handle assembly 16. For example, the proximal guidewire port 26 may be positioned about 0.1 to 10 cm or less, or about 1 to 5 centimeters or less from the proximal end of the push catheter 14. In other embodiments, the proximal guidewire port 26 may provide the delivery device 10 with single-operator-exchange (SOE) capabilities such that a shorter guidewire may be used. While not explicitly shown, other embodiments are also contemplated where the delivery device 10 is an over-the-wire (OTW) system.

The guide catheter 12 may be slidably disposed within the lumen 28 of the push catheter 14 and may extend distally from the distal end of the push catheter 14. The stent 20 may be positioned on a distal portion of the guide catheter 12 (e.g., along an outer surface of the guide catheter 12), which may be located distal of the push catheter 14, and the stent 20 may abut the distal end 30 of the push catheter 14. The delivery device 10 may also include a holding filament or suture (not shown) for releasably connecting the push catheter 14 to the stent 20. When the stent 20 has been properly placed within the anatomy, the stent 20 may be disconnected from the push catheter 14 such that the stent 20 remains in the anatomy or body lumen when the push catheter 14 is withdrawn.

The proximal end 32 of the push catheter 14 may be attached to the handle assembly 16. For example, the proximal end 32 may include a female luer lock connector 34 threadably coupled to a threaded male connector 36 of the handle assembly 16. It may be understood, however, that the push catheter 14 may be attached to the handle assembly 16 and extend distally therefrom by other means, such as adhesive bonding, welding, friction fit, interlocking fit, or other suitable means.

The guide catheter 12 may include a distal tubular portion 38 and a proximal elongate wire 40, such as a pull wire, coupled to the distal tubular portion 38. In some instances, the proximal elongate wire 40 may be a wire, filament, thread, portion of a catheter wall, fabric, web, or similar elongate structure. In some embodiments, the proximal elongate wire 40 may be coupled to the distal tubular portion 38 at a rotatable connection that may allow rotatable movement between the distal tubular portion 38 and the proximal elongate wire 40 of the guide catheter 12. The proximal elongate wire 40 may extend proximally through the lumen 28 of the push catheter 14 to the handle assembly 16. In some embodiments, the proximal elongate wire 40 may extend proximally through the handle assembly 16 to a location proximal of the handle assembly 16. In some embodiments, the proximal end of proximal elongate wire 40 may terminate at a knob 42 which may be grasped by an operator to manipulate the guide catheter 12.

As shown in FIG. 2, the proximal elongate wire 40 may share the lumen 28 of the push catheter 14 with the guidewire 2 along a portion of the length of the proximal elongate wire 40. Thus, in some embodiments, a portion of the proximal elongate wire 40 may extend proximally from the distal tubular portion 38 alongside the guidewire 2 through the lumen 28 of the push catheter 14 up to a location where the guidewire 2 exits the proximal guidewire port 26 of the push catheter 14.

Figure 3:
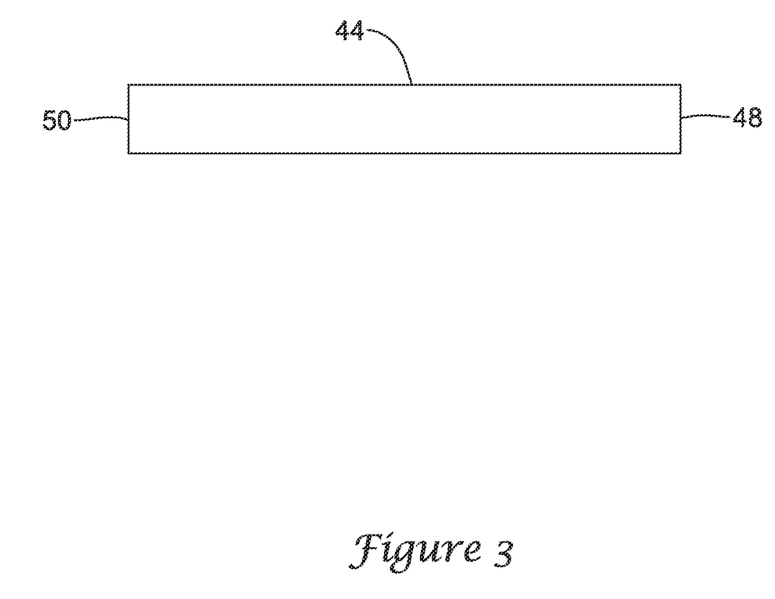
FIG. 3 is a side view of an example tubular body.

FIG. 3 illustrates an example tubular body 44, which may be used in conjunction with or otherwise be part of the delivery device 10. The tubular body 44 may include a proximal end 48 and a distal end 50. In general, the tubular body 44 may be sized and shaped so as to fit over the stent 20, the push catheter 14, and/or the delivery device 10. In other words, the inner diameter of the tubular body 44 may be about the same or slightly larger than the outer diameter of the stent 20, the push catheter 14, and/or the delivery device 10. In some embodiments, the inner diameter of the tubular body 44 may be about 0.1 to about 0.4 inches, or about 0.105 to about 0.393 inches (e.g., about 8-30 Fr), or about 0.105 to about 0.197 inches (e.g., about 8-15 Fr), or about 0.105 to about 0.131 inches (e.g., about 8-10 Fr). These are just examples.

In at least some embodiments, the tubular body 44 may have a length that is relatively short (when compared to the overall length of the delivery device 10). For example, the tubular body 44 may have a length that is shorter than the length of the stent 20 or about the same as the length of the stent 20. Other embodiments, however, are contemplated where the length of the tubular body 44 is longer. For example, the tubular body may have a length that is longer than the length of the stent 20 and/or may span substantially the full length of the push catheter 14 (and/or the full length of the delivery device 10). These are just examples.

The tubular body 44 may have several desirable uses. For example, the tubular body 44 may be used to aid of the loading of the stent 20 into another medical device 60 used with the delivery device 10. In some embodiments, the tubular body 44 may be inserted into a port 62 of the medical device 60 and the stent 20 and the delivery device 10 may thereafter be inserted into the tubular body 44.

Figure 4:
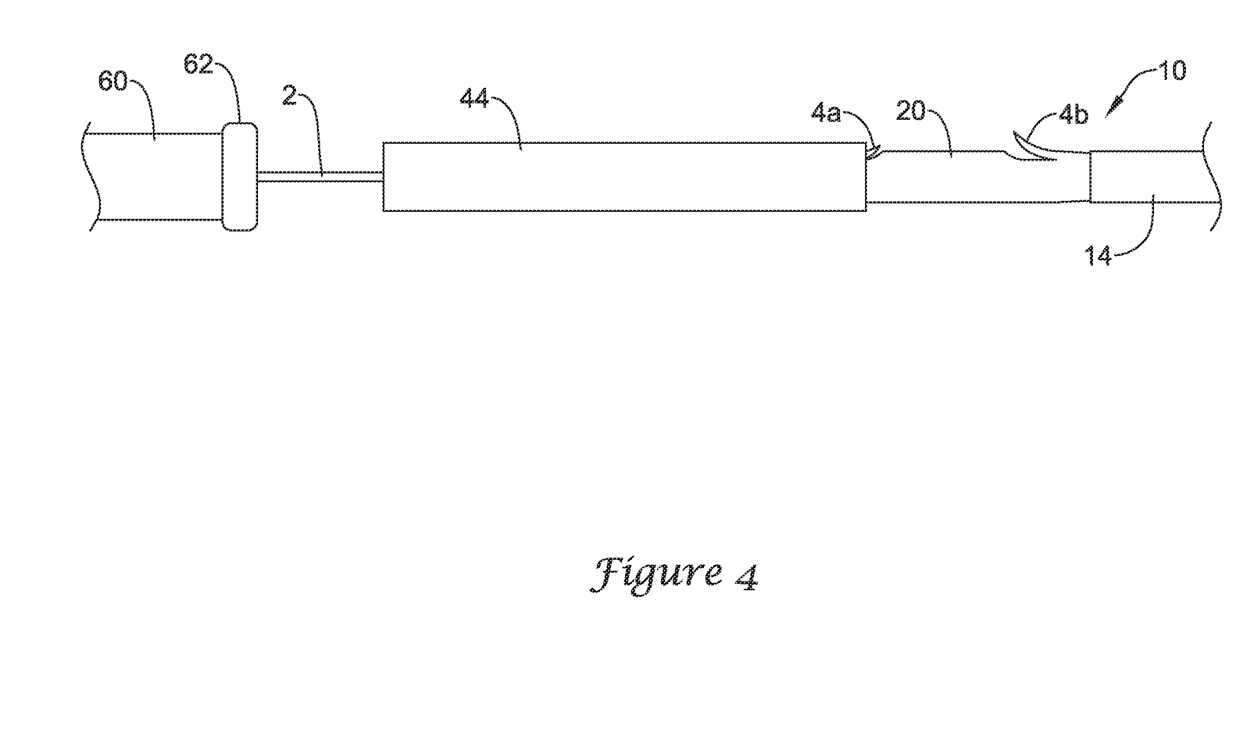
FIG. 4 is a partial side view of an example stent delivery system.

As seen in FIG. 4, the tubular body 44 may be passed over the stent 20 and the distal end of the delivery device 10 (or the stent 20 and the distal end of the delivery device 10 passed into the tubular body 44). Indeed, the tubular body 44 can be urged proximally relative to the stent 20 until it passes over the stent 20 (or the stent 20 urged distally until it passes through the tubular body 44). This may include covering and/or compressing the anchoring mechanism (e.g., flaps 4a/4b) on the stent 20, which may make it easier for the stent 20 (and/or the delivery device 10) to be advanced into another medical device 60, which may take the form of an endoscope or other suitable device. In FIG. 4, the distal flap 4a can be seen being compressed. As the tubular body 44 is urged further proximally relative to the stent 20, the tubular body 44 can also compress the proximal flap 4b of the stent 20. Alternatively, the tubular body 44 may be held substantially stationary and the delivery device 10 may be advanced therethrough.

Figure 5:
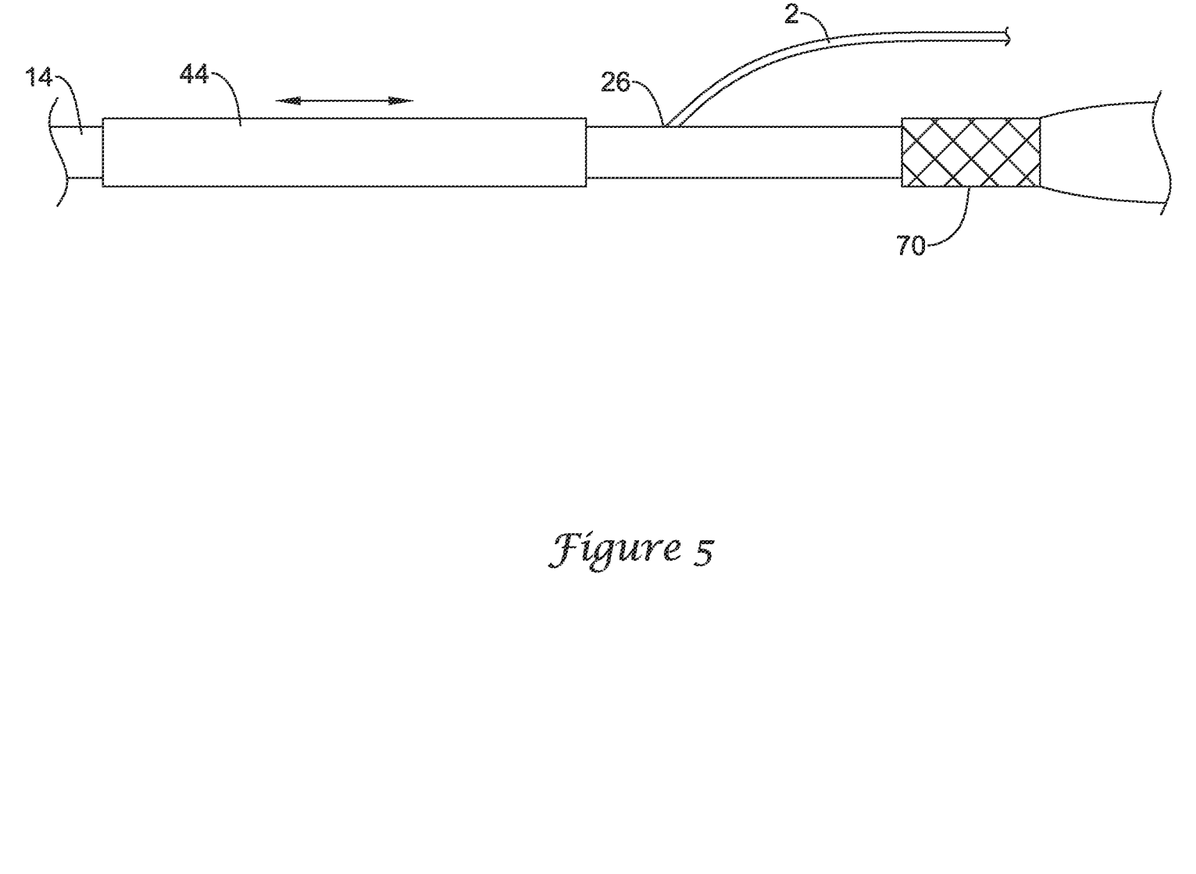
FIG. 5 is a partial side view of an example stent delivery system.

In some embodiments, the tubular body 44, following insertion of the delivery device 10 into another medical device such as an endoscope, must be removed from the port 62 to facilitate a seal between the port 62 and the delivery device 10 to prevent bodily fluid(s) (e.g., bile juice) from exiting the port 62 and/or to facilitate the use of suction during the procedure. In such embodiments, the tubular body 44, after withdrawal from the port 62, may slide freely along an outer diameter of the delivery device 10, as may be seen in FIG. 5, for example. Some practitioners may find the presence of the tubular body 44 moving along the outer diameter of the delivery device 10 to be distracting or interfering with other procedural activities. In some embodiments, for example as illustrated in FIG. 5, the proximal end 32 of the push catheter 14 and/or the proximal end of the delivery device 10 may include a constraining member 70 configured to engage the tubular body 44 at the proximal end of the delivery device 10. In some embodiments, the constraining member 70 may be positioned on or at a distal end of the handle assembly 16. In some embodiments, the constraining member 70 may be positioned on or at a distal end of the female luer lock connector 34 of the push catheter 14.

In some embodiments, the position of the tubular body 44 may be secured relative to the delivery device 10. This may be done in a number of different ways. For example, the inner diameter of the tubular body 44 may approximate the outer diameter of the delivery device 10 (e.g., the outer diameter near or at the proximal end of the delivery device 10). As such, the tubular body 44 may be frictionally engaged with and held to the delivery device 10 when positioned at the proximal end of the delivery device 10. In other embodiments, a protrusion or hub may be formed on the delivery device 10 such that the tubular body 44 may be fitted over the protrusion and be held via friction and/or an interference fit. In still other embodiments, having the guidewire 2 within the tubular body 44 may increase the friction between the tubular body 44 and the delivery device 10 or otherwise create an interference fit or bond. These are just examples. Numerous other securing relationships may be formed between the tubular body and the delivery device 10, which may secure the position of the tubular body 44 relative to the delivery device 10.

Figure 6:
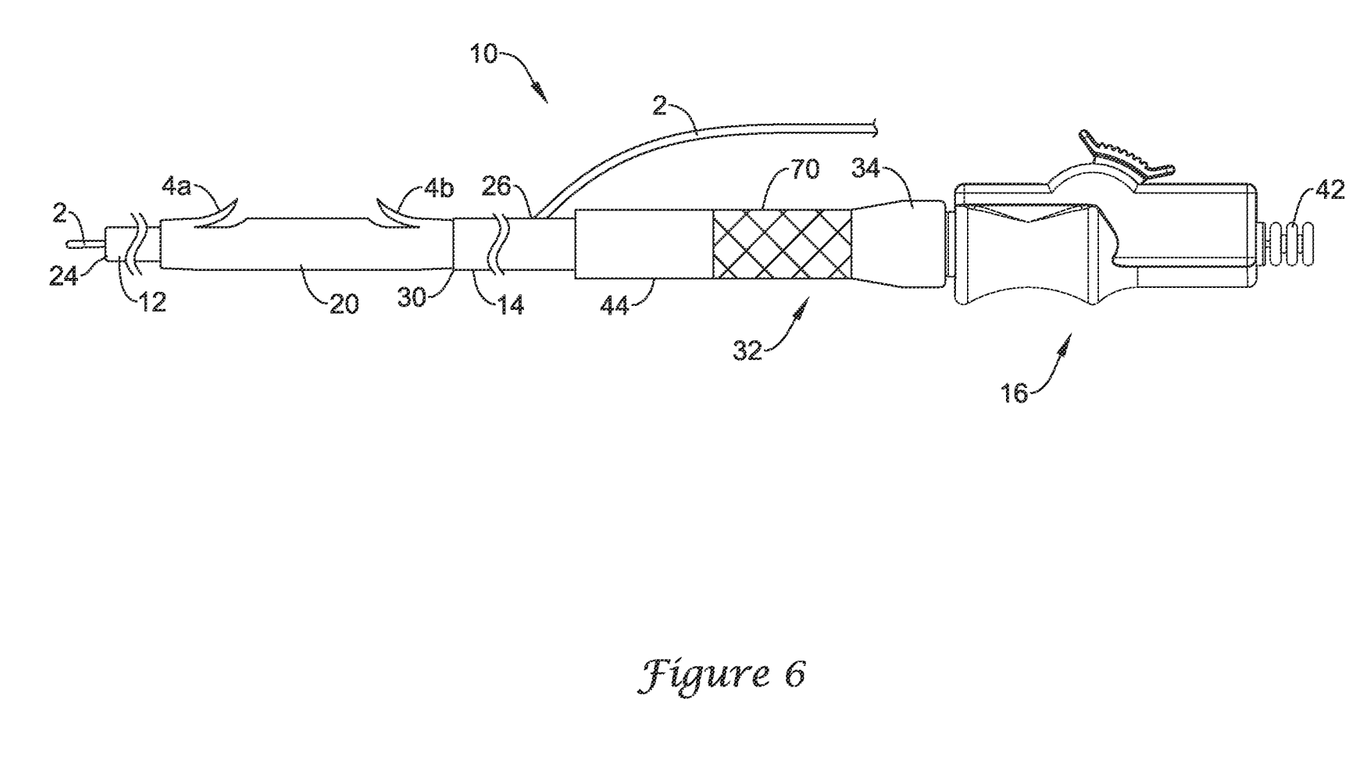
FIG. 6 is a partial side view of an example stent delivery system.

For example, as illustrated in FIG. 6, the constraining member 70 may be configured to engage an external portion of the tubular body 44. In order to achieve the configuration illustrated in FIG. 6, the tubular body 44 may be slid over the delivery device 10 proximally toward the handle assembly 16. After passing the proximal guidewire port 26, the guidewire 2 may be pulled distally through the tubular body 44, such that the tubular body 44 is positioned proximally of the guidewire 2 and the proximal guidewire port 26. The tubular body 44 may be engaged to or with the constraining member 70 at the proximal end of the delivery device 10 and/or the proximal end 32 of the push catheter 14. In some embodiments, the constraining member 70 may be configured to engage a proximal end of the tubular body 44. In some embodiments, the constraining member 70 may be configured to engage an outer surface of the tubular body 44. For example, the constraining member 70 may include a tubular sleeve sized and/or configured to create an interference fit or bond with the outer surface of the tubular body 44. Alternatively, while not expressly illustrated, in some embodiments the constraining member may include an arm, a hook, a latch, a notch, an internal protrusion, internal threads, or other feature capable of engaging an external portion of the tubular body 44 and thereby retaining the tubular body 44 at a fixed position along the outer diameter of the delivery device 10 and/or the push catheter 14.

Figure 7:
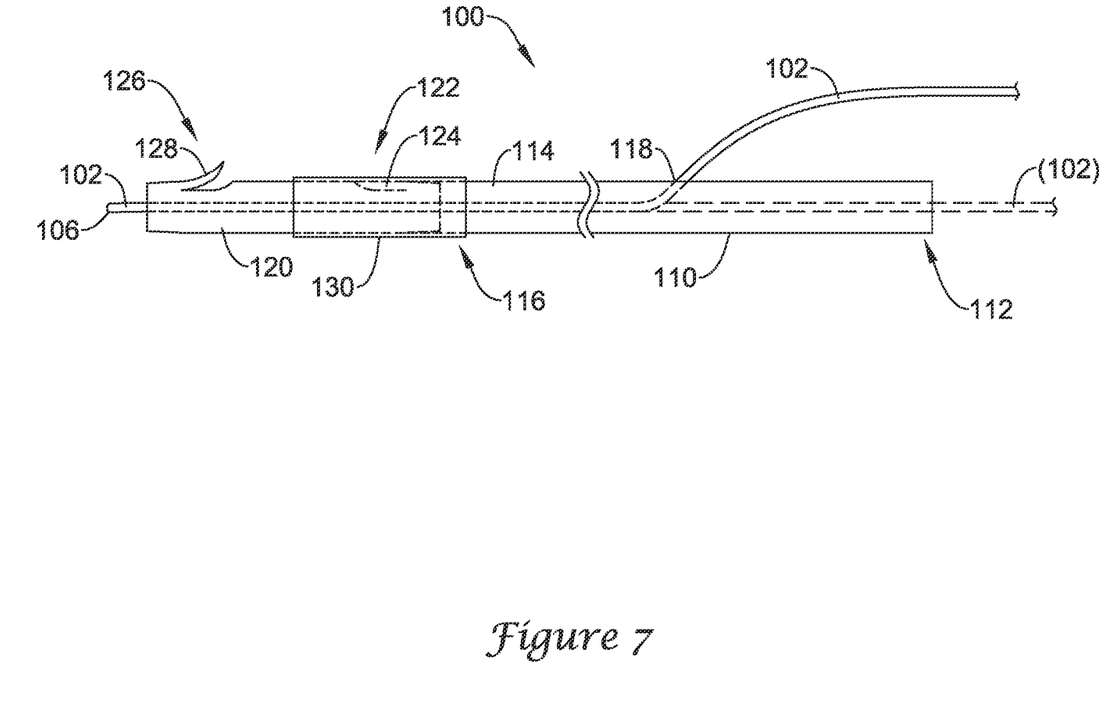
FIG. 7 is a partial side view of an example stent delivery system.

FIG. 7 illustrates an alternative drainage stent delivery system 100 including a guidewire 102 having a proximal end and a distal end 106. The delivery system 100 may include an elongate pusher shaft 110 having a proximal end 112, a distal end 116, and a lumen 114 extending therebetween. The guidewire 102 may be slidably disposed within the lumen 114. In some embodiments, the delivery system 100 may include a proximal guidewire port 118 disposed adjacent to the proximal end 112 of the elongate pusher shaft 110 such that the delivery system 100 is a "long wire" device. As the name implies, long wire devices utilize relatively long guidewires that extend along nearly the full length of the elongate pusher shaft 110 and exit the proximal guidewire port 118 near the proximal end 112 of the elongate pusher shaft 110. For example, the proximal guidewire port 118 may be positioned about 0.1 to 10 cm or less, or about 1 to 5 centimeters or less from the proximal end of the elongate pusher shaft 110. In other embodiments, the proximal guidewire port 118 may provide the delivery system 100 with single-operator-exchange (SOE) capabilities such that a shorter guidewire may be used. Other embodiments are also contemplated where the delivery system 100 is an over-the-wire (OTW) system, as seen in phantom in FIG. 7.

The delivery system 100 may include a drainage stent 120 having an anchoring mechanism, the anchoring mechanism including a proximal portion 122 having at least one distally-facing flap 124 and a distal portion 126 having at least one proximally-facing flap 128. The flap(s) 124 and 128 may be similar to flap(s) 4b and 4a, respectively, discussed above. The drainage stent 120 may be positioned in abutting contact with the distal end 116 of the elongate pusher shaft 110. The drainage stent 120 may have an outer diameter that is similar to an outer diameter of the elongate pusher shaft 110. A tubular body 130 may have an inner surface mated to and fixedly attached to an outer surface of the elongate pusher shaft 110 at the distal end 116, for example, by adhesive bonding, welding, friction fit, interlocking fit, or other suitable means. The tubular body 130 may extend distally of the distal end 116. The tubular body 130 may have an inner diameter about the same or slightly larger than the outer diameter of the elongate pusher shaft 110 and/or the drainage stent 120. In some embodiments, the inner diameter of the tubular body 130 may be about 0.1 to about 0.4 inches, or about 0.105 to about 0.393 inches (e.g., about 8-30 Fr), or about 0.105 to about 0.197 inches (e.g., about 8-15 Fr), or about 0.105 to about 0.131 inches (e.g., about 8-10 Fr). These are just examples. The tubular body 130 may cover the proximal portion 122 of the anchoring mechanism. The tubular body 130 may provide support to the drainage stent 120, thereby preventing axial compression or collapse of the drainage stent 120 at the proximal portion 122 as the drainage stent 120 is delivered to the target site. The drainage stent 120 may be configured to slide distally within the tubular body 130 following delivery of the drainage stent 120 to a target site.

In use, a guidewire 102 may be inserted intraluminally and the distal end 106 navigated to a target site. The elongate pusher shaft 110 and drainage stent 120 may be inserted over the guidewire 102 intraluminally and/or into a lumen of another medical device, such as an endoscope, disposed on the guidewire 102. The elongate pusher shaft 110, and the drainage stent 120 positioned within the tubular body 130, may be advanced distally to the target site. Upon approaching the target site, exact positioning of the drainage stent 120 may be determined by appropriate an imaging or locating method. After positioning the drainage stent 120 at the target site, the elongate pusher shaft 110 may with be withdrawn proximally. The distal portion 126 of the anchoring mechanism is not be covered by the tubular body 130. As such, at the target site, the at least one proximally-facing flap 128 may be in frictional and/or interfering contact with tissue at the target site. As the elongate pusher shaft 110 is withdrawn, the at least one proximally-facing flap 128 prevents the drainage stent 120 from withdrawing from the target site along with the elongate pusher shaft 110. As the elongate pusher shaft 110 is withdrawn, the proximal portion 122 of the anchoring mechanism is exposed to surrounding tissue. Once the drainage stent 120 is deployed, the anchoring mechanism prevents axial movement of the drainage stent 120. The elongate pusher shaft 110 and the guidewire 102 may be withdrawn from the patient. Accordingly, no additional components are necessary to place the drainage stent 120 at the target site.

The materials that can be used for the various components of the delivery device 10/100 and/or the tubular body 44/130 disclosed herein may include those commonly associated with medical devices. For simplicity purposes, the following discussion makes reference to the delivery device 10, the push catheter 14, and the tubular body 44. However, this is not intended to limit the devices and methods described herein, as the discussion may be applied to any of the other structures and/or components of the delivery devices disclosed herein.

The tubular body 44 and/or other components of the delivery device 10 may be made from a metal, metal alloy, polymer (some examples of which are disclosed below), a metal-polymer composite, ceramics, combinations thereof, and the like, or other suitable material. Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

The tubular body 44 and/or other components of the delivery device 10 may include a support and/or reinforcing structure incorporated therein such as, for example, a braid, a coil, a mesh, supporting fillers and/or amalgams, or the like. In addition, the tubular body 44 and/or other components of the delivery device 10 may include cuts, slots, holes, openings, or the like formed therein, which may increase flexibility.

In at least some embodiments, portions or all of the push catheter 14 and/or other components of the delivery device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the delivery device 10 in determining its location. Some examples of radiopaque materials can include, but are not limited to, gold, platinum, palladium, tantalum, tungsten alloy, polymer material loaded with a radiopaque filler, and the like. Additionally, radiopaque marker bands and/or coils may also be incorporated into the design of the delivery device 10 to achieve the same result.

In some embodiments, a degree of Magnetic Resonance Imaging (MRI) compatibility is imparted into the delivery device 10. For example, to enhance compatibility with MRI machines, it may be desirable to make the push catheter 14, or other portions of the delivery device 10, in a manner that would impart a degree of MRI compatibility. For example, the push catheter 14, or portions thereof, may be made of a material that does not substantially distort the image and create substantial artifacts (i.e., gaps in the image). Certain ferromagnetic materials, for example, may not be suitable because they may create artifacts in an MRI image. The push catheter 14, or portions thereof, may also be made from a material that the MRI machine can image successfully. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

The tubular body 44 and/or other components of the delivery device 10 may be made from or otherwise include a polymer or polymeric material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the polymer can be blended with a liquid crystal polymer (LCP). For example, the mixture can contain up to about 6 percent LCP.

In some embodiments, an exterior surface of the delivery device 10 may be sandblasted, beadblasted, sodium bicarbonate-blasted, electropolished, etc. In these as well as in some other embodiments, a coating, for example a lubricious, a hydrophilic, a protective, or other type of coating may be applied over portions or all of the delivery device 10. In some embodiments, the lumen of the tubular body 44 may include a lubricious, hydrophilic, protective, or other similar coating disposed on an inner surface thereof. Hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as high-density polyethylene (HDPE), polytetrafluoroethylene (PTFE), polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference.

The coating and/or sheath may be formed, for example, by coating, extrusion, co-extrusion, interrupted layer co-extrusion (ILC), gradient extrusion, or fusing several segments end-to-end. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

The arrangement of the various structures of the delivery device 10 may vary. In some embodiments, the delivery device 10 may include any of the structures or utilize any of the arrangements of structures that are disclosed in U.S. Pat. Nos. 5,152,749; 5,334,185; 5,921,952; 6,248,100; 6,264,624; and 6,562,024, the entire disclosures of which are herein incorporated by reference.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A drainage stent delivery system, comprising:
    a drainage stent delivery device including a distal end and a handle disposed at a proximal end thereof; and
    a tubular body having a proximal end, a distal end, and a lumen extending therebetween, the lumen being sized to slidably fit about an outer diameter of the delivery device and an outer diameter of a drainage stent having an anchoring mechanism, the drainage stent disposed at the distal end of the delivery device;
    wherein the delivery device includes a constraining member configured to form an interference fit with an external portion of the tubular body at the proximal end of the delivery device.

2. The drainage stent delivery system of claim 1, wherein the anchoring mechanism includes one or more flaps formed in the stent.

3. The drainage stent delivery system of claim 1, wherein the constraining member is configured to engage the proximal end of the tubular body.

4. The drainage stent delivery system of claim 1, wherein the constraining member is configured to engage an outer surface of the tubular body.

5. The drainage stent delivery system of claim 1, wherein when the tubular body is positioned distal of the constraining member, the tubular body freely slides along the outer diameter of the delivery device.

6. The drainage stent delivery system of claim 5, wherein when the constraining member is engaged with the tubular body, the tubular body is fixed in position along the outer diameter of the delivery device.

7. The drainage stent delivery system of claim 1, wherein the stent is disposed about a guide catheter.

8. The drainage stent delivery system of claim 7, wherein a push catheter is disposed about the guide catheter and positioned adjacent to the stent.

9. The drainage stent delivery system of claim 8, wherein the guide catheter and the push catheter are configured to extend through an endoscope.

10. A method of delivering a drainage stent, comprising:
inserting an endoscope including a port proximate a proximal end thereof into a patient;
inserting a distal end of a tubular body into the port;
inserting a distal end of a drainage stent delivery device and a drainage stent having an anchoring mechanism disposed at the distal end of the delivery device into the tubular body;
wherein the delivery device includes a handle disposed at a proximal end thereof and includes a constraining member configured to form an interference fit with an external portion of the tubular body and retain the tubular body at the proximal end of the delivery device;
wherein the tubular body includes a lumen sized to slidably fit about an outer diameter of the delivery device and an outer diameter of the drainage stent having an anchoring mechanism;
advancing the drainage stent distally through the tubular body;
sliding the tubular body proximally toward the handle; engaging an external portion of the tubular body with the constraining member.

11. The method of claim 10, wherein the constraining member is configured to engage the proximal end of the tubular body.

12. The method of claim 10, wherein the constraining member is configured to engage an outer surface of the tubular body.

13. The method of claim 10, wherein the anchoring mechanism includes one or more flaps formed in the stent.

14. The method of claim 10, wherein forming an interference fit with an external portion of the tubular body and the constraining member includes inserting a proximal end of the tubular body into a distal end of the constraining member.

15. The method of claim 10, wherein advancing the drainage stent distally through the tubular body includes pushing the drainage stent with a push catheter disposed about a guide catheter, the drainage stent being disposed about the guide catheter.

16. The method of claim 10, wherein when the tubular body is positioned distal of the constraining member, the tubular body freely slides along the outer diameter of the delivery device.

17. The method of claim 10, wherein when the constraining member is engaged with the tubular body, the tubular body is fixed in position along the outer diameter of the delivery device.

18. The method of claim 15, wherein the guide catheter and the push catheter are configured to extend through the endoscope.

* * * * *